United States Patent [19]

Johnson et al.

[11] 4,397,700
[45] Aug. 9, 1983

[54] PIPERAZINE DERIVATIVES OF FERROCENE

[75] Inventors: Nancy C. Johnson, Waldorf; Carl Gotzmer, Accokeek; Mark Graff, Crofton, all of Md.

[73] Assignee: The United States of America as represented by the Secretary of the Navy, Washington, D.C.

[21] Appl. No.: 351,711

[22] Filed: Feb. 24, 1982

[51] Int. Cl.$^3$ .............................................. C06B 45/34
[52] U.S. Cl. ...................................... 149/7; 149/19.2; 544/225
[58] Field of Search ............................ 149/7, 8, 19.2; 544/225, 358

[56] References Cited

U.S. PATENT DOCUMENTS 3,765,965  10/1973  Van Landuyt et al. ................. 149/7
3,874,957   4/1975  Corley et al. ........................... 149/7
4,352,700  10/1982  Hoffman .............................. 149/19.2

OTHER PUBLICATIONS

Nielson et al., *J. Org. Chem.*, 41, 655-659, (1976).

Primary Examiner—Edward A. Miller

[57] ABSTRACT

Diferrocenyl piperazines represented by the formula:

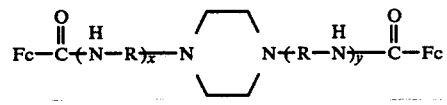

wherein Fc represents a ferrocene radial R represents alkylene radical having from 1 to 7 carbon atoms, and x and y are 0 or 1 are disclosed as burning rate modifiers for ammonium perchlorate composite propellants. Coating ammonium perchlorate crystals with the diferrocenyl piperazines significantly decreases migration of the piperazines in the propellant.

9 Claims, No Drawings

PIPERAZINE DERIVATIVES OF FERROCENE

BACKGROUND OF THE INVENTION

The invention pertains generally to composite propellants and in particular to burning rate modifiers for ammonium perchlorate composite propellants.

Ferrocenes are used in solid rocket propellants as effective burning rate catalysts for ammonium perchlorate (AP)-based systems. Ferrocene and its derivatives are very rapidly oxidized in the burning propellant to iron oxide particles of submicron size which act as catalytic sites to accelerate the gas-phase decomposition of perchloric acid (formed from decomposing AP). In addition to rate enhancement, ferrocene compounds are useful in reducing the dependence of burning rate on pressure for fast burning propellants.

The development and use of ferrocene and its derivatives in solid propellants have presented several problems. Ferrocene is a rather high-melting solid that sublimes at moderate temperatures. It cannot be used in propellants because of its tendency to migrate through the propellant grain and crystallize at the surface. Use of liquid alkyl ferrocenes, such as those disclosed in A. T. Nielson et al. J. Org. Chem. 41 p. 655–9 1976 has eliminated the crystallization problem, allowed better dispersion of iron throughout the propellant, and provided better processing qualities by acting as a plasticizer. Unfortunately, most of the alkyl ferrocenes are sufficiently volatile for significant quantities to be lost during processing and for sensitivity hazards to arise due to contact with ammonium perchlorate dust in the mixer. These additives migrate badly in the cured propellant and are easily oxidized because of their alpha-hydrogen structure. Ease of oxidation and migration are responsible for increased sensitivity and erratic burning in propellants.

Large, nonvolatile, nonreactive multi-ferrocene molecules, such as those disclosed in Carl Gotzmer et al. *Non-Migrating Ferrocene Modifiers for Composite Propellants.* 1979 JANNAF Propulsion Meeting, Vol. II, PP 475–83, March 1979, were developed to overcome migration and processing problems. These were thought to be less likely to migrate through the propellant grain because of greater chain entanglement with the binder. Aging studies, however, indicated that migration and oxidation problems still existed but to a lesser degree. For example, aging data for a series of CTBN propellants prepared using one weight percent of bis (2-ferrocenylethyl) disulfide, which is retained by the propellant binder polymer via chain entanglement and polar forces, indicated that plasticizers played a major role in the ferrocene compound's migratory aptitude and that its use should be restricted to propellants containing no plasticizer and to storage conditions below 60° C.(140° F.).

Recent efforts have centered on chemically bonding ferrocene derivatives to the propellant matrix. Such a procedure would ensure that the burning rate modifier remains uniformly distributed throughout the propellant while retaining its catalytic effectiveness. Aging qualities of the propellant would thereby be much improved over those where accelerators are not chemically bonded. Various approaches have been used to react ferrocene additives with certain components of a propellant formulation.

Binders have been prepared which contain ferrocene as an integral part of the polymer. For example, copolymers of vinyl ferrocene and butadiene, disclosed in U.S. Pat. No. 3,886,190 by S. F. Reed, issued on May, 1975, have been used as binders for ammonium perchlorate-based propellant systems and have produced burning rate increases of about 20 percent. Other examples of ferrocene-polymers used as propellant binders are disclosed in U.S. Pat. No. 4,168,362 by Gotzmer et al and U.S. Pat. No. 3,886,007 by Combs, Jr. et al. Difficulties, however, have been encountered in obtaining high ferrocene-content polymers that retain good mechanical properties.

Incorporation of ferrocene into the binder matrix via the curing agent also ensures nonmigration and complete dispersion of the modifier. For example, ferrocene derivatives containing hydroxyl and/or isocyanate functional groups, can be joined to a HTPB binder network via crosslinking binder network via crosslinking and chain extending. Migration of ferrocenes tied to the binder matrix by this method has been proven to be non-existent. However, the quantity of ferrocene incorporated into the propellant formulation is limited by the stoichiometry of the crosslinking system.

Coating ammonium perchlorate with certain tertiary-amine derivatives, e. g. aziridinylmethyl ferrocene (AMF) of H. M. Fisher *Multipurpose Additives for Composite Propellants.* RK-TR-69-6. PP 10–12, May, 1969 (declassified on 1972), 1-pyrrolidinylmethyl ferrocene (PMF) of O. E. Ayers et al. *Multipurpose Additives for Composite Propellants, Part II.* RR-TR-70-8. PP 1–5 March, 1970, (declassified on 1973), and N, N-dimethylaminomethylferrocene (DAMF) of C. Gotzmer et al., ibid, decreases migration. The main disadvantages of AMF are that (1) the aziridinyl group can interfere with the propellant binder cure reaction (therefore, quantities that can be used are limited), and (2) AMF-coated AP is extremely impact, friction, and thermally sensitive when dry. The sensitivity and safety problems of AMF are also found with the other two ferrocenes.

SUMMARY OF THE INVENTION

It is, therefore, an object of the present invention to prepare ferrocenyl derivatives with a high iron content, a low sensitivity, a high oxidation resistance, and a low cost.

Another object of this invention is to prepare ferrocenyl derivatives which can be added to a propellant during processing.

And another object of this invention is to prepare ferrocenyl derivatives which do not interfere with binder cure and do not decrease the mechanical properties of a cured propellant containing the ferrocenyl derivatives.

A further object of this invention is to prepare a ferrocenyl derivative which can form a complex with ammonium perchlorate.

These and other objects are achieved by a multiferrocenyl tertiary-amine derivative with no $\alpha$-hydrogens on the ferrocenyl-substituted carbon atom and with a low vapor pressure, which can be prepared with few steps in high yields from inexpensive reactants.

DETAILED DESCRIPTION OF THE INVENTION

The multiferrocenyl tertiary-amine derivatives of this invention are represented by the formula:

wherein Fc represents a ferrocene radical, R represents an alkylene radical, and x and y are 0 or 1. The preferred alkylene radicals are straight and branched and have from one to seven carbon atoms; the most preferred alkylene radicals have from one to four carbon atoms.

The subject ferrocenes can be easily and inexpensively prepared by admixing ferrocene carbonyl chloride with piperazine or a substituted derivative thereof in a non-reactive polar solvent at a temperature from about 20° to about 50° C. and separating the product from the reaction solution. The preferred solvent is tetrahydrofuran. The preferred reaction temperature is from 22° to 30° C.

Having described the ferrocenes of this invention and their preparation, the following examples are given as specific illustrations thereof. It is understood that these examples are given by way of illustration and are not meant to limit this disclosure or the claims to follow in any manner.

Infrared spectra for compound characterization and reaction progress data were obtained using Beckman Acculab 9 and Perkin-Elmer Model 180 spectrophotometers. Proton NMR spectra were obtained on a Varian EM 390 instrument.

Thermogravimetric studies were carried out using a DuPont 990 Thermal Analyzer and a 951 Thermogravimetric Module.

EXAMPLE I

Synthesis of 1,4-Diferrocenoyl Piperazine

A solution of crude ferrocene carbonyl chloride (5.5 g, 0.03 mol) in 50 ml of tetrahydrofuran was treated with a solution of piperazine (3.44 g, 0.04 mol) in 50 ml of tetrahydrofuran. After allowing the reaction mixture to stand at room temperature for a day, the precipitate was collected by suction filtration. The crude amide was purified from 1:1 solution of ethanol and water to give 5.0 g of crystalline material, mp 252° C. $^1$H NMR (CDCl$_3$) δ4.37 (t,4, substituted cyclopentadienyl), 4.15 (t,4, substituted cyclopentadienyl), 4.03 (s, 10, unsubstituted cyclopentadienyl), 3.58 (s, 8, piperazine ring). IR (KBr) 1634 cm−1 (tertiary amide C=O).

Theoretical (calcd for C$_{26}$H$_{26}$Fe$_2$N$_2$O$_2$): 61.21%C; 5.10%H; 5.49%N; 21.91%Fe; Experimental: 61.34%C; 5.26%H; 5.49%N; 21.86%Fe.

EXAMPLE II

Synthesis of 1-(N-Ferrocenoyl-2-Aminoethyl)-4-Ferrocenoyl Piperazine

A solution of ferrocene carbonyl chloride (5.5 g, 0.03 mol) in 50 ml of tetrahydrofuran was treated with a solution of N-2-aminoethyl piperazine (3.87 g, 0.03 mol) in 50 ml of tetrahydrofuran. After allowing the reaction mixture to stand at room temperature for a day, the precipitate was collected by suction filtration. The crude amide was purified by recrystallization from a 75% aqueous ethanol solution to give 6.2 g of crystalline material: mp, 190°-191° C.; IR (kBr) 3500-3300 (secondary amide NH), 1640-1620 (both secondary and tertiary amide C=O), 1545-1530 cm−1 (amide NH). Solvation problems were encountered in obtaining the $^1$H NMR spectrum of this compound; it may be necessary to use $^{13}$C NMR to complete structural elucidation of this compound.

Theoretical (calcd for C$_{28}$H$_{31}$Fe$_2$N$_3$O$_2$): 60.79%C; 5.61%H; 7.60%N; 20.21%Fe; Experimental: 60.76%C; 5.66%H; 7.53%N; 20.16%Fe.

The volatilization rate constants in min$^{-1}$ and the half life of volatilization at 65.5° C. and 25 mm vacuum were measured for the above two examples. The results are compared with other ferrocene compounds in Table I.

TABLE 1

| VOLATILIZATION DATA FOR FERROCENYL COMPOUNDS | | |
|---|---|---|
| Compound | −log K | T$_{0.5}$ |
| Ferrocene aldehyde dimethylhydrazone | 1.93 | 1 hour |
| Ferrocenyl(dimethylaminoethyl)ketone | 2.34 | 2.5 hours |
| 1-Ferrocenoyl-4-methyl piperazine | 5.19 | 74 days |
| 1,4-Diferrocenoyl piperazine | 8.71 | >1 year |
| 1-(N—Ferrocenoyl-2-aminoethyl)-4-ferrocenoyl piperazine | 9.45 | >1 year |

Standard coating techniques can be utilized in coating ammonium perchlorate, but solvent processes are preferred from safety considerations. The preferred method comprises dissolving the subject ferrocene in tetrahydrofuran or a similar solvent and contacting crystals of ammonium perchlorate with the solution. The complexing reaction occurs quickly and easily. The ferrocenes of this invention act both as a burning rate modifier and a bonding agent for ammonium perchlorate.

Obviously, many modifications and variations of the present invention are possible in light of the above teachings. It is therefore to be understood that, within the scope of the appended claims, the invention may be practiced otherwise than as specifically described.

What is claimed is:

1. A diferrocenyl piperazine represented by the formula:

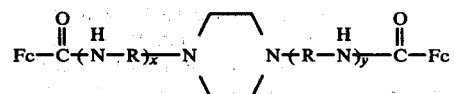

where Fc represents a ferrocene radical, R represents an alkylene radical, and x and y are 0 or 1.

2. The diferrocenyl piperazine of claim 1 wherein R is a straight or branched alkylene radical having from 1 to 7 carbon atoms.

3. The diferrocenyl piperazine of claim 2 wherein R is a straight or branched alkylene radical having from 1 to 4 carbon atoms.

4. The diferrocenyl piperazine of claim 1 wherein x and y are 0.

5. The diferrocenyl piperazine of claim 2 wherein x is 1 and y is 0.

6. The diferrocenyl piperazine of claim 5 wherein R represents a alkylene radical having from 1 to 4 carbon atoms.

7. Ammonium perchlorate coated with a diferrocenyl piperazine represented by the formula:

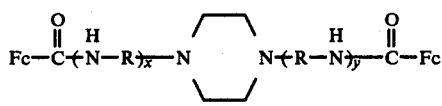
where Fc represents a ferrocene radical, R represents an alkylene radical having from 1 to 7 carbon atoms, and x and y are 0 or 1 wherein said piperazine is complexed with ammonium perchlorate.
8. The diferrocenyl piperazine coated ammonium perchlorate of claim 7 wherein x and y are 0.
9. The diferrocenyl piperazine coated ammonium perchlorate of claim 7 wherein x is 0 and y is 1.
* * * * *